(12) United States Patent
Sra

(10) Patent No.: US 7,311,705 B2
(45) Date of Patent: Dec. 25, 2007

(54) CATHETER APPARATUS FOR TREATMENT OF HEART ARRHYTHMIA

(75) Inventor: Jasbir S. Sra, Pewaukee, WI (US)

(73) Assignee: Medtronic, Inc., Minneapolis, MN (US)

( * ) Notice: Subject to any disclaimer, the term of this patent is extended or adjusted under 35 U.S.C. 154(b) by 494 days.

(21) Appl. No.: 10/916,662

(22) Filed: Aug. 12, 2004

(65) Prior Publication Data

US 2005/0038333 A1 Feb. 17, 2005

Related U.S. Application Data

(63) Continuation-in-part of application No. 10/353,625, filed on Jan. 29, 2003, now Pat. No. 6,926,714.

(60) Provisional application No. 60/531,293, filed on Dec. 19, 2003, provisional application No. 60/494,607, filed on Aug. 12, 2003, provisional application No. 60/354,561, filed on Feb. 5, 2002.

(51) Int. Cl.
*A61B 18/18* (2006.01)

(52) U.S. Cl. ........................ 606/41; 607/122

(58) Field of Classification Search ............... 606/41, 606/48–50; 607/101, 102, 122
See application file for complete search history.

(56) References Cited

U.S. PATENT DOCUMENTS 3,954,098 A    5/1976  Dick et al.

(Continued)

FOREIGN PATENT DOCUMENTS

| EP | 1182619 A2 | 2/2002 |
|---|---|---|
| EP | 1321101 A2 | 12/2002 |
| GB | 2 239 802 A | 7/1991 |
| WO | WO 91/07726 | 5/1991 |
| WO | WO 96/10949 | 4/1996 |

OTHER PUBLICATIONS

C.L. Grines et al.; "Functional Abnormalities in Isolated Left Bundle Branch Block: The Effect of Interventricular Asynchrony;" *Circulation*; 1989; 79:845-53.

(Continued)

*Primary Examiner*—Michael Peffley
(74) *Attorney, Agent, or Firm*—Jansson Shupe & Munger Ltd.

(57) ABSTRACT

A catheter apparatus is provided for use in the treatment of heart arrhythmia having a catheter shaft, a mapping and ablation catheter disposed within the shaft, and a control mechanism coupled to both the shaft and catheter. The catheter shaft includes a main body and a coaxial tip section joined to the main body. The tip section can be rotated about a central axis and curved away from the central axis in a controlled manner. The mapping and ablation catheter can be extended outward from the catheter shaft where it is able to take the form of a pre-stressed curve. The control mechanism controls axial rotation of the tip section, the degree of deflection of the tip section and longitudinal movement of the mapping and ablation catheter with respect to the catheter shaft. Preferably, the mapping and ablation catheter forms a pre-stressed loop when it is fully extended from the catheter shaft.

In another aspect of this invention, it provides a method for treatment of a heart arrhythmia having the steps of (1) obtaining cardiac image data from a medical imaging system, (2) creating a 3D model from this cardiac image data, (3) registering the 3D model to an interventional system, (4) positioning a catheter apparatus within a chamber of the heart, (5) displaying the catheter apparatus over the registered 3D model on the interventional system, (6) navigating the catheter apparatus within the heart guided by the registered 3D model, and (7) having the catheter apparatus ablate heart tissue at select locations.

17 Claims, 11 Drawing Sheets

U.S. PATENT DOCUMENTS

| | | | |
|---|---|---|---|
| 4,547,892 A | 10/1985 | Richey et al. | |
| 4,574,807 A | 3/1986 | Hewson et al. | |
| 4,660,571 A | 4/1987 | Hess et al. | |
| 4,807,621 A | 2/1989 | Hagen et al. | |
| 4,940,064 A | 7/1990 | Desai | |
| 5,245,282 A | 9/1993 | Mugler, III et al. | |
| 5,245,287 A | 9/1993 | Nowak et al. | |
| 5,255,679 A | 10/1993 | Imran | |
| 5,274,551 A | 12/1993 | Corby, Jr. | |
| 5,304,212 A | 4/1994 | Czeisler et al. | |
| 5,341,807 A | 8/1994 | Nardella | |
| 5,348,020 A | 9/1994 | Huston | |
| 5,353,795 A | 10/1994 | Souza et al. | |
| 5,391,199 A | 2/1995 | Ben-Haim | |
| 5,431,688 A | 7/1995 | Freeman | |
| 5,464,447 A | 11/1995 | Fogarty et al. | |
| 5,568,384 A | 10/1996 | Robb et al. | |
| 5,575,766 A | 11/1996 | Swartz et al. | |
| 5,575,772 A | 11/1996 | Lennox | |
| 5,582,609 A * | 12/1996 | Swanson et al. | 606/39 |
| 5,595,183 A * | 1/1997 | Swanson et al. | 600/510 |
| 5,611,777 A | 3/1997 | Bowden et al. | |
| 5,636,634 A * | 6/1997 | Kordis et al. | 600/534 |
| 5,642,736 A | 7/1997 | Avitall | |
| 5,676,662 A | 10/1997 | Fleischhacker et al. | |
| 5,702,438 A | 12/1997 | Avitall | |
| 5,720,775 A | 2/1998 | Larnard | |
| 5,730,704 A | 3/1998 | Avitall | |
| 5,738,096 A | 4/1998 | Ben-Haim | |
| 5,807,249 A | 9/1998 | Qin et al. | |
| 5,823,958 A | 10/1998 | Truppe | |
| 5,829,447 A | 11/1998 | Stevens et al. | |
| 5,839,440 A | 11/1998 | Liou et al. | |
| 5,846,254 A | 12/1998 | Schulze et al. | |
| 5,871,532 A | 2/1999 | Schroeppel | |
| 5,931,811 A | 8/1999 | Haissaguerre et al. | |
| 5,951,475 A | 9/1999 | Gueziec et al. | |
| 5,954,692 A | 9/1999 | Smith et al. | |
| 6,079,414 A | 6/2000 | Roth | |
| 6,081,577 A | 6/2000 | Webber | |
| 6,086,581 A | 7/2000 | Reynolds et al. | |
| 6,154,516 A | 11/2000 | Heuscher et al. | |
| 6,233,304 B1 | 5/2001 | Hu et al. | |
| 6,234,804 B1 | 5/2001 | Yong | |
| 6,235,038 B1 | 5/2001 | Hunter et al. | |
| 6,241,728 B1 * | 6/2001 | Gaiser et al. | 606/41 |
| 6,249,693 B1 | 6/2001 | Cline et al. | |
| 6,252,924 B1 | 6/2001 | Davantes et al. | |
| 6,254,568 B1 | 7/2001 | Ponzi | |
| 6,256,368 B1 | 7/2001 | Hsieh et al. | |
| 6,266,553 B1 | 7/2001 | Fluhrer et al. | |
| 6,289,115 B1 | 9/2001 | Takeo | |
| 6,289,239 B1 | 9/2001 | Panescu et al. | |
| 6,311,693 B1 | 11/2001 | Sterman et al. | |
| 6,314,310 B1 | 11/2001 | Ben-Haim et al. | |
| 6,325,797 B1 | 12/2001 | Stewart et al. | |
| 6,348,034 B1 | 2/2002 | Thompson | |
| 6,348,793 B1 | 2/2002 | Balloni et al. | |
| 6,350,248 B1 | 2/2002 | Knudson et al. | |
| 6,353,445 B1 | 3/2002 | Babula et al. | |
| 6,381,485 B1 | 4/2002 | Hunter et al. | |
| 6,383,151 B1 | 5/2002 | Diederich et al. | |
| 6,389,104 B1 | 5/2002 | Bani-Hashemi et al. | |
| 6,394,948 B1 | 5/2002 | Borst et al. | |
| 6,401,720 B1 | 6/2002 | Stevens et al. | |
| 6,411,848 B2 | 6/2002 | Kramer et al. | |
| 6,421,412 B1 | 7/2002 | Hsieh et al. | |
| 6,423,051 B1 | 7/2002 | Kaplan et al. | |
| 6,456,867 B2 | 9/2002 | Reisfeld | |
| 6,468,265 B1 | 10/2002 | Evans et al. | |
| 6,478,028 B1 | 11/2002 | Paolitto et al. | |
| 6,478,803 B1 | 11/2002 | Kapec et al. | |
| 6,485,455 B1 | 11/2002 | Thompson et al. | |
| 6,490,475 B1 | 12/2002 | Seeley et al. | |
| 6,490,479 B2 | 12/2002 | Bock | |
| 6,502,576 B1 | 1/2003 | Lesh | |
| 6,503,247 B2 | 1/2003 | Swartz et al. | |
| 6,520,953 B1 | 2/2003 | Schultz | |
| 6,527,769 B2 | 3/2003 | Lasngberg et al. | |
| 6,546,270 B1 | 4/2003 | Goldin et al. | |
| 6,549,606 B1 | 4/2003 | Vaillant et al. | |
| 6,556,695 B1 | 4/2003 | Packer et al. | |
| 6,572,612 B2 | 6/2003 | Stewart et al. | |
| 6,584,343 B1 | 6/2003 | Ransbury et al. | |
| 6,606,113 B2 | 8/2003 | Nakamura | |
| 6,610,058 B2 | 8/2003 | Flores | |
| 6,612,980 B2 | 9/2003 | Chen et al. | |
| 6,614,595 B2 | 9/2003 | Igarashi | |
| 6,616,655 B1 | 9/2003 | Falwell et al. | |
| 6,628,743 B1 | 9/2003 | Drummond et al. | |
| 6,628,976 B1 | 9/2003 | Fuimaono et al. | |
| 6,629,987 B1 | 10/2003 | Gambale et al. | |
| 6,632,223 B1 | 10/2003 | Keane | |
| 6,650,927 B1 | 11/2003 | Keidar | |
| 6,711,428 B2 | 3/2004 | Fuimaono et al. | |
| 6,733,499 B2 | 5/2004 | Scheib | |
| 6,782,284 B1 | 8/2004 | Subramanyan et al. | |
| 6,795,721 B2 | 9/2004 | Coleman et al. | |
| 7,187,963 B2 * | 3/2007 | Coleman et al. | 600/374 |
| 2002/0010392 A1 | 1/2002 | Desai | |
| 2002/0042570 A1 | 4/2002 | Schaldach et al. | |
| 2002/0046756 A1 | 4/2002 | Laizzo et al. | |
| 2002/0138105 A1 | 9/2002 | Kralik | |
| 2003/0018251 A1 | 1/2003 | Solomon | |
| 2003/0023266 A1 | 1/2003 | Borillo et al. | |
| 2003/0028183 A1 | 2/2003 | Sanchez et al. | |
| 2003/0097219 A1 | 5/2003 | O'Donnell et al. | |
| 2003/0187358 A1 | 10/2003 | Okerlund et al. | |
| 2003/0220557 A1 | 11/2003 | Cleary et al. | |
| 2004/0087850 A1 | 5/2004 | Okerlund et al. | |
| 2004/0138714 A1 | 7/2004 | Daum et al. | |
| 2004/0225212 A1 | 11/2004 | Okerlund et al. | |
| 2004/0225328 A1 | 11/2004 | Okerlund et al. | |
| 2004/0225331 A1 | 11/2004 | Okerlund et al. | |

OTHER PUBLICATIONS

H.B. Xia et al., "Differing effects of right ventricular pacing and left bundle branch block on left ventricular function;" *Br. Heart J.*, 1993; 69:166-73.

S. Cazeau et al., "Effects of Multisite Biventricular Pacing in Patients with Heart Failure and Intraventricular Conduction Delay;" *N. Engl. J. Med.* 2001; 344:873-880.

M.V. Pitzalis et al., "Cardiac Resynchronization Therapy Tailored by Echocardiographic Evaluation of Ventricular Acnchrony;" *J. Am. Coll. Cardiol.* 2002; 40:1615-22.

W.T. Abraham et al., "Cardiac Resynchronization in Chronic Heart Failure;" *N. Engl. J. Med.* 2002; 346:1845-1853.

W.M. Feinberg et al.; "Prevalence, Age Distribution, and Gender of Patients with Atrial Fibrillation;" *Arch. Intern. Med.* vol. 155; Mar. 1995; pp. 469-473.

J.L. Cox, J.P. Boineau, R.B. Schuessler, T.B. Ferguson, Jr., M.E. Cain, B.D. Lindsay, P.B. Corr, K.M. Kater, D.G. Lappas; "Operations for Atrial Fibrillation;" Electrophysiology, Pacing and Arrhythmia, Clin. Cardiol. 14, 1991; pp. 827-834.

M.Haissaguerre, P. Jais, S.C. Shah, A. Takahashi, M. Hocini, G. Quiniou, S. Garrigue, A. LeMouroux, P. Le Metayer, and J. Clementy; "Spontaneous Initiation of Atrial Fibrillation by Ectopic Beats Originating in the Pulmonary Viens;" The New England Journal of Medicine, vol. 339, No. 10, Sep. 3, 1998; pp. 659-668.

C. Pappone, S. Rosanio, G. Augello, G. Gallus, G. Vicedomini, P. Mazzone, S. Gulletta, F. Gugliotta, A. Pppone, V. Santinelli, V. Tortoriello, S. Sal, A. Zangrillo, G. Crescenzi, S. Benussi, and O. Alfieri; "Mortality, Morbidity, and Quality of Life After Circumferential Pulmonary Vein Ablation for Atrial Fibrillation;" Journal of the American College of Cardiology, vol. 42, No. 2; 2003; 185-197.

J. Sra et al., "Current Problems in Cardiology—Atrial Fibrilliation: Epidemiology, Mechanisms, and Management;" Current Problems in Cardiology, Jul. 2000; pp. 406-524.

ACC/AHA/ESC Practise Guidelines; Eur. Heart J., vol. 22, Issue 20, Oct. 2001; pp. 1854-1923.

M.D. Leash, T. Trepelse, H. Omran, A. Bartorelli, P. Della Bella, T. Nakai, M. Reisman, D. Fleschenberg, U. Krumsdorf, and D. Scherer; "Tiny Device Blocks 'Usless' Part of Heart, prevents blood clots;" Journal Report; American Heart Association; Apr. 9, 2002.

H. Nikagawa et al., "Role of the Tricuspid Annulus and the Eustachian Valve/Ridge on Atrial Flutter: Relevance to Catheter Ablation of the Septal Isthmus and a New Technique for Rapid Identification of Ablation Success;" Circulation 1996; 94:407-24.

L. Gepstein et al., "A Novel Method for Nonfluoroscopic Catheter-Based Electroanatomical Mapping of the Heart: In Vitro and In Vivo Accuracy Results;" Circulation 1997; 95:1611-22.

S.Shpun et al., "Guidance of Radiofrequency Endocardial Ablation with Real-time Three-dimensional Magnetic Navigation System;" Circulation 1997; 96:2016-21.

J. Sra et al., "Electroanatomic Mapping to Identify Breakthrough Sites in Recurrent Typical Human Flutter;" Paceing Clin. Electrophysiol 2000; 23:1479-92.

R.J. Schilling et al.; "Simultaneous Endocardial Mapping in the Human Left Ventricle Using a Noncontact Catheter: Comparison of Contact and Reconstructed Electrograms During Sinus Thythm;" Circulation 1998; 98:997-98.

C.C. Gornick et al., "Validation of a New Noncontact Catheter System for Electroanatomic Mapping of Left Ventricular Endocardium;" Circulation 1999; 99:829-835.

J. Sra et al., "Noncontact Mapping for Radiofrequency Ablation of Complex Cardiac Arrhythmias;" J. Interven. Cardiac Electrophysiol 2001; 5:323-331.

N. M.S. de Groot et al., "Three-Dimensional Catheter Positioning During Radiofrequency Ablation in Patients: First Application of a Real-Time Position Management System;" J. Interven. Cardiac Electgrophysiol 2001; Nov. 11(11):1183-92.

J. Schreieck et al., "Radiofrequency Ablation of Cardiac Arrhythmias Using a Three-Dimensional Real-Time Position Management and Mapping System;" Pacing Clin. Electrophysiol, Dec. 2002 25(12):1699-707.

F. Wittkampf et al., "Real-time, Three-Dimensioanl, Nonfluoroscopic Localization of the Lasso Catheter;" J Interven. Cardiac Electrophysiol, 2002, 13:630.

J. Sra et al., "Cardiac Chamber Geometry Construction, Catheter Navication and Ablation Using Cutaneous Patches;" Supplement to Circulation Oct. 2003, 108 (17):IV-585, Abstract 2667.

J. Sra et al., "Three-Dimensional Right Atrial Geometry Construction and Catheter Tracking Using Cutaneous Patches;" Interven. Cardiac Electrophysiol, 2003 14: 897.

Z. Zhang; "Iterative Point Matching for Regitration of Free-Form Curves;" Inria 1992, pp. 1-40.

C.A. Pelizzari et al., "Accurate Three-Dimensional Registration of CT, PET, and/or MR Images of the Brain;" J. Comput. Assist. Tomogr. 1989; 13:20-26.

A.C. Evans et al.; "MRI-PET Correlation in Three Dimensions Using a Volume-of-Interest (VOI) Atlas;" J. Cerb Flow Metab. 1991; 11:A69-A78.

R.P. Woods et al.; "Rapid Automated Algorithm for Aligning and Reslicing PET Images;" Journal of Computer Assisted Tomography, 1992; 16:620-633.

B.A. Ardekani et al.; "A Fully Automatic Multimodality Image Registration Algorithm;" Journal of Computer Assisted Tomography; 1995; 19:615-623.

L. Thurfell et al.; "Registration of Neuroimaging Data: Implementation and Clinic Applications;" American Society of Neuroimaging; 2000; 10:39-46.

S.A. Ben-Haim et al.; "Nonfluoroscopic, in vivo navigation and mapping technology;" Nature Medicine; 1996, 2:1393-5.

B. Taccardi et al.; "A new intracaitary probe for detecting the site of origin of ectopic ventricular beats during one cardiac cycle;" Circulation; 1987; 75:272-81.

F.H.M. Wittkampf et al.; "New Technique for Real-Time 3-Dimensional Localization of Regular Intracardiac Electrodes;" Circulation; 1999; 99:1312-17.

V. Fuster et al. "ACC/AHA/NASPE 2002 Guidelines Update for Implantation of Pacemakers and Antiarrhythmia Devices;" J. Am. Coll. Cardiol 2001; 38:1-47.

D. R. Ney "Volumetric Rendering of Computed Tomography Data: Principles and Techniques;" IEEE Computer Graphics and Application; 1990; 24-32.

N. M. Alpert et al., "The Principal Axes Transformation—A Method for Image Registration;" The Journal of Nuclear Medicine; 1990; 31:1717-1722.

P.A. van den Elsen et al.; "Medical Image Matching—A Review with Classification;" IEEE Engineering in Medicine and Biology, 1993; 26-38.

G. T. Barnes et al.; "Conventional and Spiral Computed Tomography: Physical Principles and Image Quality Considerations;" Computed Body Tomography, 1998, Lippincot-Raven, Philadelphia, PA pp. 1-20.

"Advanced Vessel Analysis" prouct description [online] http://www.gehealthcare.com/usen/ct/clin_app/products/aswessel.html [retrieved Dec. 1, 2004].

"CardilQ" product description [online], http://egems.gehealthcare.com/geCommunity/Europe/flex_trial/awFlexTrial/aw3_1/eflextrial [retrieved Dec. 1, 2004].

"Current Problems in Cardiology—Atrial Fibrillation: Epidemiology, Mechanisms, and Management;" Current Problemsn Cardiology, Jul. 2000; pp. 406-524.

Jasbir Sra, M.D., F.A.C.C. "Synchronized Registration of Three-Dimensioanl Left Atrial Computerized Tomographic Images with Cardiac Mapping: Validation of Registration Procedure", Circulation,vol. 108, No. 17, Oct. 28, 2003.

Jasbir Sra, M.D. "Synchronized Registration of Three-Dimensional Left Atrial Images in Atrial Fibrillation", Pacing And Clinical Electgrophysiology, Apr. 2003, vol. 26, No. 4, Part II, pp. 929-1173.

PCT Search Report for PCT/US2004/020909.

PCT International Search Report, File Reference P23682.02, International Application No. PCT/US2005/030868, International Filing Date Aug. 31, 2005 (5 pages).

Milan Sonka and J. Michael Fitzpatrick (eds); Handbook of Medical Imaging vol. 2. Medical Image Processing and Analysis: pp. 129-174 & 447-506, Jun. 15, 2002.

\* cited by examiner

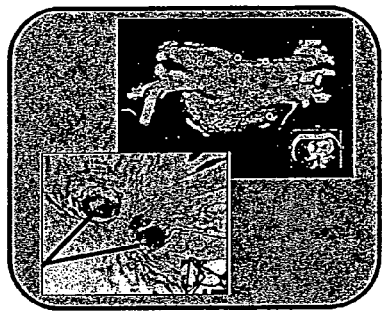 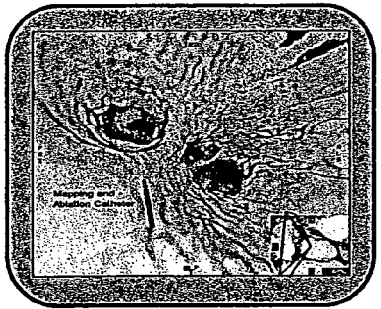 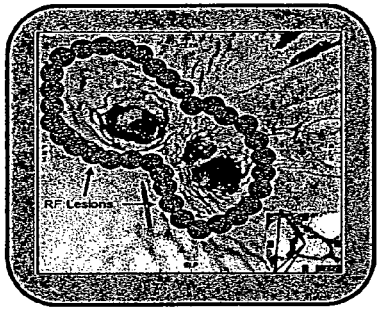
Registration of 3D and Endocardial Images on the Interventional System
Visualization of Catheter Over the CT Image
Isolation of Pulmonary Veins-Areas Ablated by the Catheter are Shown by Circular Tags
FIG. 4A    FIG. 4B    FIG. 4C
 
FIG. 5

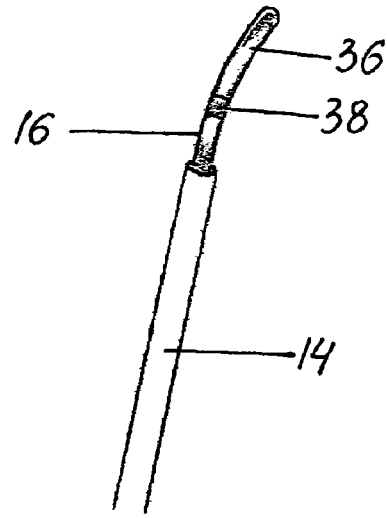
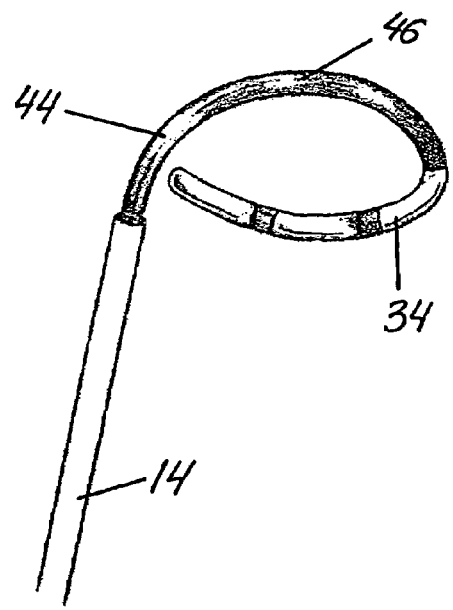
FIG. 8A  FIG. 8B
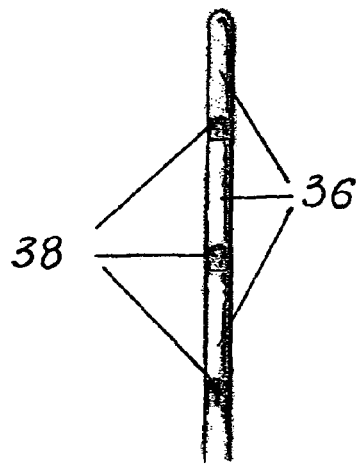
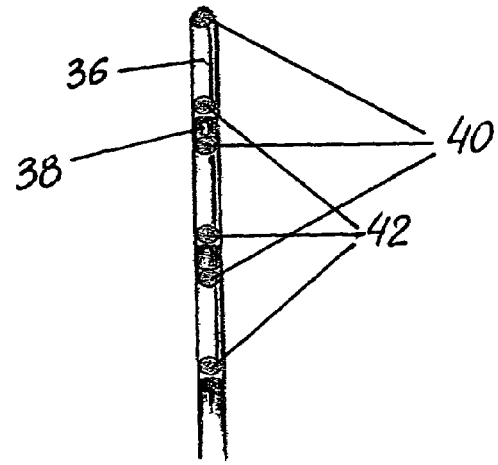
FIG. 9A  FIG. 9B

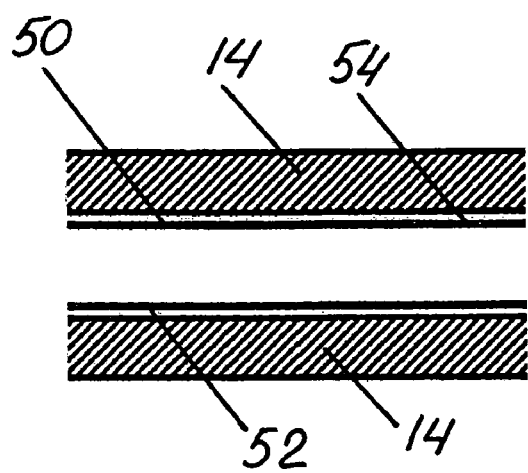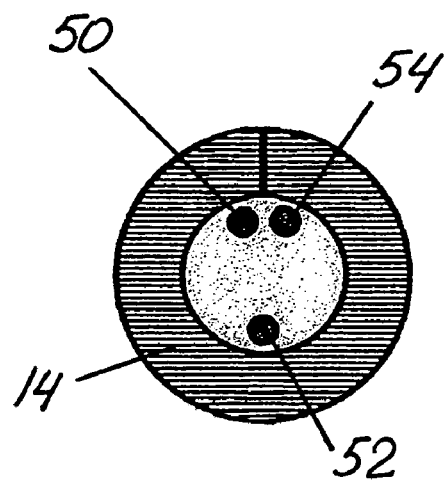
FIG. 10A  FIG. 10B

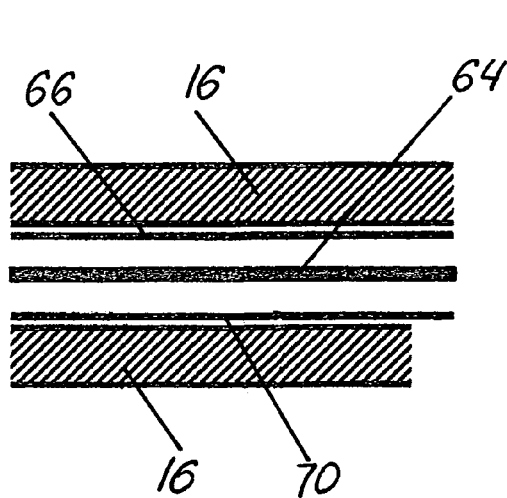
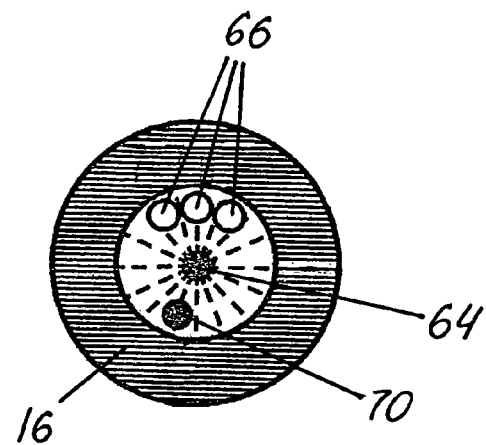
FIG. 14A  FIG. 14B
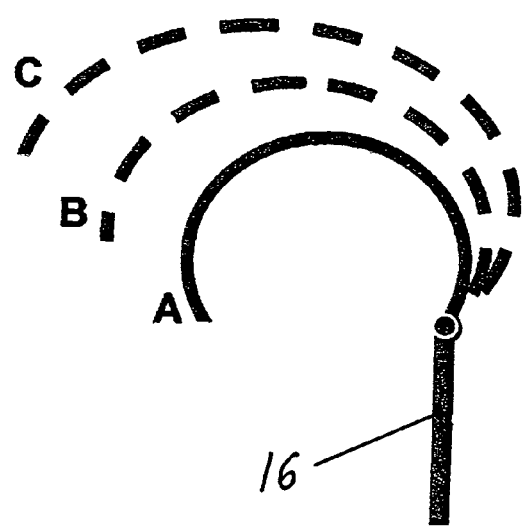
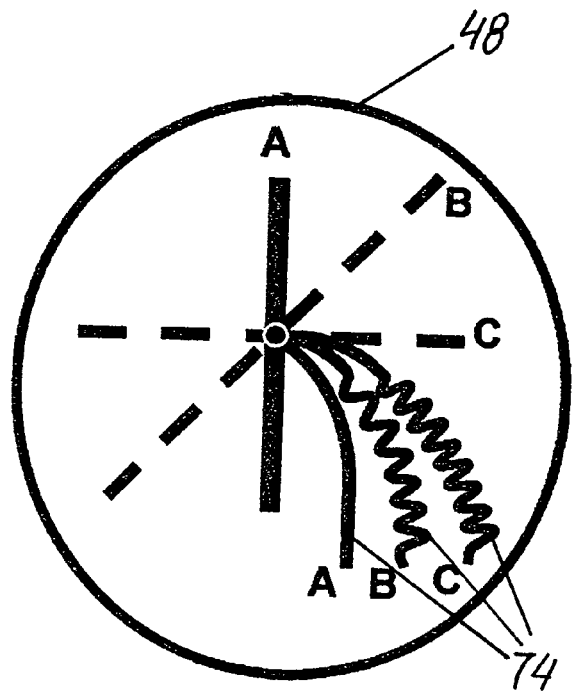
FIG. 15A  FIG. 15B

CATHETER APPARATUS FOR TREATMENT OF HEART ARRHYTHMIA

RELATED APPLICATION

This application is a continuation-in-part of U.S. patent application Ser. No. 10/353,625, filed on Jan. 29, 2003, now U.S. Pat. No. 6,926,714, which claims the benefit of U.S. Provisional Application No. 60/354,561, filed on Feb. 5, 2002, and claims the benefit of U.S. Provisional Application No. 60/494,607, filed on Aug. 12, 2003, and U.S. Provisional Application No. 60/531,293 filed on Dec. 19, 2003.

FIELD OF THE INVENTION

This invention relates generally to catheter apparatus and methods for treatment of heart arrhythmia and, in particular, to catheter apparatus that conform to the anatomy of the left atrium for pulmonary vein isolation and for ablation of other left atrial structures in patients with atrial fibrillation.

BACKGROUND OF THE INVENTION

Heart rhythm problems or cardiac arrhythmias are a major cause of mortality and morbidity. An example of different rhythm problems encountered in clinical practice include atrial fibrillation (AF), cardiac arrest or sudden cardiac death (SCD) due to ventricular tachycardia/ventricular fibrillation (VT/VF), atrial flutter and other forms of atrial and ventricular arrhythmias. During the past 20 years, cardiac electrophysiology has evolved into a clinical tool to diagnose these cardiac arrhythmias. During electrophysiology studies multipolar catheters are positioned inside the heart and electrical recordings are made from the different chambers of the heart. Careful study of surface ECG and data from intracavitary electrograms is used conventionally to treat these arrhythmias.

Atrial fibrillation (AF), where the atria (upper chambers of the heart) stop contracting as they fibrillate or quiver, is the most common of the heart rhythm problems encountered in clinical practice. Recent data suggests AF is the most common arrhythmia-related cause of hospital admissions. Estimates indicate that 2.2 million people in the United States alone have AF and that 160,000 new cases are diagnosed every year. Patients with AF have a high incidence of such complications as stroke, and heart failure and bear an ominous prognosis of higher overall and cardiovascular mortality.

Recently it has been shown that premature atrial contractions can act as triggers and initiate paroxysms of AF. These premature ectopic beats have been shown to originate predominantly in the pulmonary veins. Inability to reproducibly identify the precise location of these trigger sites limits catheter ablation of trigger sites of AF.

Because of the critical role of the pulmonary veins in the generation of AF, and as infrequent and nonreproducible premature atrial contractions limit the utility of trigger site ablation, a variety of surgical and nonsurgical catheter ablation techniques have been used to isolate the pulmonary veins from the left atrium. An energy source such as radio-frequency waves are used to create a series of small scars on the heart's surface near the connection between the pulmonary veins and the left atrium. These scars stop the erratic impulses of atrial fibrillation by directing the impulses towards a normal electrical pathway through the heart.

Other strategic areas such as between the mitral annulus and the pulmonary veins, between the pulmonary veins, and between the left pulmonary veins and the left atrial appendage can also be targeted for ablation to increase the success rate in treating AF. Complete isolation of the pulmonary veins using various energy sources in patients undergoing open heart surgery has led to successful termination of AF in over 80% of patients. Although less invasive, trying to replicate this procedure non-surgically however is lengthy and labor intensive.

Sudden cardiac death is defined as an unexpected natural death from cardiac causes within a short period of time. Most SCDs are caused by VT/VF. It is estimated that SCD accounts for approximately 300,000 cardiac deaths in the United States alone each year. SCD is the most common and often the first manifestation of coronary artery disease and may be responsible for approximately 50% of deaths from cardiovascular disease in the United States. The most commonly encountered form of VT typically originates in the vicinity of a healed myocardial infarction. The mechanism of VT is reentry associated with myocardial scarring. However, these reentrant circuits are quite broad because of the nature of the scarring. The success rate of VT ablation would increase considerably if it were possible to precisely interrupt these broad reentrant circuits using lesions that transect them.

Several other arrhythmias such as atrial flutter, atrial tachycardias, and tachycardias involving accessory connections between the atria and ventricles are also extremely common and cause significant morbidity and some risk of higher mortality. Ablation between the tricuspid annulus and inferior vena cava, forming an anatomical barrier around the flutter circuit, can terminate atrial flutter. Similarly, the crista terminalis in the right atrium is a common source of atrial tachycardia. In this and other arrhythmias, the ability to precisely locate and identify these areas and to have a catheter apparatus that conforms to the particular 3D anatomy of each site so that ablation at that location is performed quickly and effectively would help significantly.

As specific locations such as the left atrium-pulmonary vein junction cannot be seen on fluoroscopy, multipolar catheters are usually positioned inside a heart chamber such as the left atrium after going through a blood vessel. These catheters are then swept around the cardiac chamber to gather electrophysiological information. The cardiac activation map acquired with such electrical readings is used to guide the catheters to specific locations showing double potentials. Such locations are suggestive of being sites capable of conducting impulses as between the pulmonary veins and the left atrium. Energy is then delivered by the catheters to ablate these locations.

Although helpful in certain instances, the inability to accurately relate the electrophysiologic information obtained to a specific anatomical location within the heart limits the usefulness of the readings to treat complex arrhythmias such as AF. The image created with the information is not an exact replication of the anatomy of these specific locations in the cardiac chamber. Moreover, the degree of resolution of this image is totally operator-dependent and limited by the time available to acquire the corresponding data points.

Current approaches of mapping and ablation, through their use of the currently available catheters to perform a point-by-point ablation within a complex 3D structure such as the left atrium guided by fluoroscopy and other techniques, makes the resulting ablation cumbersome, lengthy and inadequate. Since the true anatomy of the heart chamber is not being visualized, the unavailability of information on the size and orientation of such cardiac structures as the pulmonary veins and the pulmonary vein ostia contributes to the difficulty of such approaches. Given these limitations, the success rate of this procedure is low and only a limited number of patients may qualify for such treatment.

A number of modalities presently exist for improved medical diagnostic imaging. The most common ones for delineating anatomy include computed tomographic imaging (CT), magnetic resonance imaging (MRI) and x-ray systems. CT is both fast and accurate in collecting volumes of data over short acquisition times. This data has allowed for the 3D reconstruction of the underlying images into true and more understandable anatomic models. An approach that uses such 3D models for visualizing specific cardiac chambers and that provides endocardial (navigator or inside) views of such chambers to assist in the ablation of heart tissue at select locations would be highly desirable.

There is a need therefore for a catheter apparatus that can conform to the 3D anatomy of the pulmonary vein-left atrial junction and to other strategic areas in the heart so as to successfully more precisely and easily isolate the pulmonary veins and these other sites that initiate and sustain heart arrhythmias. There is also a need for a method that utilizes such catheter apparatus and allows for the visualization of the apparatus as it moves over a 3D model depicting the anatomy of a cardiac chamber such as the left atrium. Such a method would enable the rapid encircling of the pulmonary veins with a series of accurately placed lesions using radio-frequency or other forms of energy such as microwave, cryo-ablation and laser.

SUMMARY OF THE INVENTION

This invention is for a catheter apparatus used in the treatment of heart arrhythmia, preferably atrial fibrillation, having a catheter shaft, a mapping and ablation catheter and a control mechanism. The catheter shaft includes a main body and a coaxial tip section joined to the main body. The tip section is rotatable and capable of being selectively deflected away from its central axis whereby it can be curved in a controlled manner, preferably 180° to the right and to the left of the axis, coplanar with the axis. The ablation catheter is disposed within the catheter shaft and is pre-stressed to take a curved shape when it is slidably extended outward from the shaft. The control mechanism is coupled to both the catheter shaft and the ablation catheter and it controls rotation of the tip section, the degree of deflection of the tip section and axial movement of the ablation catheter with respect to the catheter shaft.

In certain preferred embodiments, the ablation catheter, when fully extended from the catheter shaft, substantially defines a plane that is perpendicular to the distal end of the tip section. More preferred is where the ablation catheter forms a loop when fully extended from the shaft. It is highly desirable that the loop have a diameter ranging from 10 mm. to 20 mm. One most preferred embodiment finds that the control mechanism also controls the diameter of the loop.

Another desirable embodiment is where the control mechanism is a steering handle having a first actuator mechanically connected to the catheter shaft and a second actuator mechanically connected to the ablation catheter. The first actuator can independently rotate the catheter shaft about its axis and deflect the tip section away from the central axis. The second actuator can move the ablation catheter axially within the catheter shaft and can also independently control the diameter of the loop formed by the ablation catheter. Most desirable is where the ablation catheter includes a spline, preferably where the spine is fabricated from a shape memory alloy such as nickel-titanium.

Certain preferred embodiments find that the ablation catheter includes an electrode section at its distal end. This electrode section has a number of electrodes, each electrode able to ablate the heart tissue with which it is brought into contact. More preferred is where at least two of the electrodes can be operated independently of each other. A most desirable embodiment finds each pair of these electrodes is separated by a section or portion that is non-ablating. Highly desirable is where each electrode has both a temperature recording site and an electrogram recording site.

In another aspect of this invention, it provides a method for treatment of a heart arrhythmia in a patient. This method includes the steps of (1) obtaining cardiac image data by using a medical imaging system; (2) creating a 3D model from this cardiac image data; (3) registering the resulting 3D model with an interventional system; (4) positioning a catheter apparatus inside one of the chambers of the heart; (5) displaying the catheter apparatus over the registered 3D model upon the interventional system; (6) navigating the catheter apparatus within the heart by utilizing the registered 3D model; and (7) ablating heart tissue at select locations with the catheter apparatus.

Certain embodiments of this method find the medical imaging system used to be a computer tomography (CT) system. Most preferred is where the method also includes the step of visualizing the 3D model over a computer workstation with the interventional system.

In more desirable cases, the heart arrhythmia being treated is atrial fibrillation and the 3D model is therefore of the left atrium and pulmonary veins. Most desirable is where the 3D model specifically includes anterior, posterior, right anterior oblique and left anterior oblique views of the left atrium. Highly preferred in these cases is where the method also includes the step of creating endocardial views of the pulmonary veins from the cardiac image data so that the orientation and size of the pulmonary veins can be identified.

Another preferred embodiment is where the catheter apparatus includes a catheter shaft, a mapping and ablation catheter slidably disposed within the catheter shaft, and a steering handle. The catheter shaft has a rotatable and deflectable tip section. The ablation catheter includes an electrode section where each electrode can ablate heart tissue and the section is pre-stressed to form a loop when fully extended outward from the catheter shaft. The steering handle controls the selective rotation of the tip section, the selective deflection of the tip section and the selective axial movement of the ablation catheter.

Most desirable is where the ablation catheter also includes a spline, preferably a spline that is fabricated from nickel-titanium having shape memory. Also preferred is where the tip section can deflect 180° either to the right or to the left within a plane coplanar with the central axis. A highly preferred embodiment finds the loop having a selectively variable diameter that is controlled by the steering handle.

One very preferred embodiment of this method includes the step of extending the electrode section outward from the catheter shaft such that the electrodes are positioned in contact with the area of the heart to be ablated and the step of actuating the electrodes to ablate in a desired manner. Most desirable is where each of these electrodes is independently operable. It is highly preferred that the actuating step include the selective activation of the electrodes.

In certain embodiments of the ablation catheter, each electrode includes a temperature recording site and an electrogram recording site. Most preferred is where the navigating step utilizes intracardial recordings of electrical activity within the heart that are taken by an electrode and then displayed by the interventional system.

One very desirable case finds the loop formed by the electrode section defining a plane substantially perpendicular to the distal end of the tip section. More preferred is the embodiment where the steering handle includes a first actuator that controls the rotation and the deflection of the shaft's tip section and a second actuator that controls the longitudinal movement of the ablation catheter and the size of the diameter of the loop formed by the ablation catheter.

It is most preferred that the method of this invention also include the steps of deflecting the tip section to a desired orientation, rotating the catheter shaft so that the tip section is positioned adjacent to the strategic area of the heart to be ablated, fully extending the ablation catheter from the catheter shaft, and adjusting the diameter of the loop. Highly desirable is where the strategic area is a junction of a pulmonary vein with the left atrium and the diameter of the loop is selected so that the ablation catheter can circumferentially isolate the pulmonary vein.

BRIEF DESCRIPTION OF THE DRAWINGS

FIG. 4A depicts 3D cardiac images of the left atrium.

FIG. 4B illustrates localization of a standard mapping and ablation catheter over an endocardial view of the left atrium registered upon an interventional system.

FIG. 4C illustrates point by point ablation using a standard catheter over the registered endocardial view in FIG. 4B.

FIG. 5 is a series of schematic views depicting a catheter apparatus in accordance with this invention positioned within the left atrium at the left atrial-pulmonary vein junction.

FIG. 8A is a side view depicting a mapping and ablation catheter in accordance with this invention extending outward from the catheter shaft.

FIG. 8B is a side view similar to FIG. 8A depicting the catheter fully extended from the catheter shaft.

FIG. 9A is a detailed view of the mapping and ablation catheter in FIGS. 8A and 8B.

FIG. 9B is a longitudinal cross-section of the mapping and ablation catheter in FIG. 9A.

FIG. 10A is a schematic view of a longitudinal cross-section of the catheter shaft.

FIG. 10B is a schematic view of a radial cross-section of the catheter shaft.

FIG. 14A is a schematic view of a longitudinal cross-section of the catheter.

FIG. 14B is a schematic view of a radial cross-section of the catheter.

FIGS. 15A and 15B are a series of schematic views depicting the changing of the diameter of the curve of the catheter as controlled by the steering handle.

DETAILED DESCRIPTION OF PREFERRED EMBODIMENTS

Figure 1:
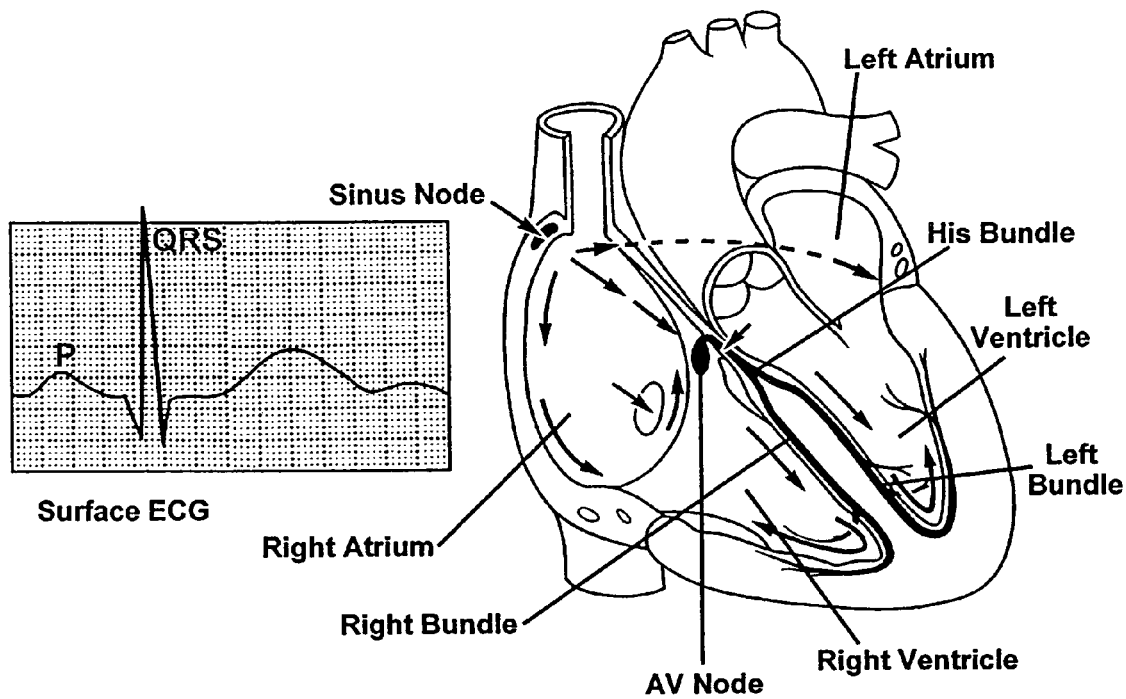
FIG. 1 is a schematic view of the heart illustrating normal electrical conduction.

FIG. 1 illustrates the normal electrical conduction in the heart. An electrical impulse starts in the sinus node and depolarizes or activates both atria. This is depicted as a P wave on the surface ECG. Following this, the impulse travels to both ventricles via the AV node and bundle of His. Ventricular activation or depolarization is depicted as QRS complex on the surface ECG.

Figure 2:
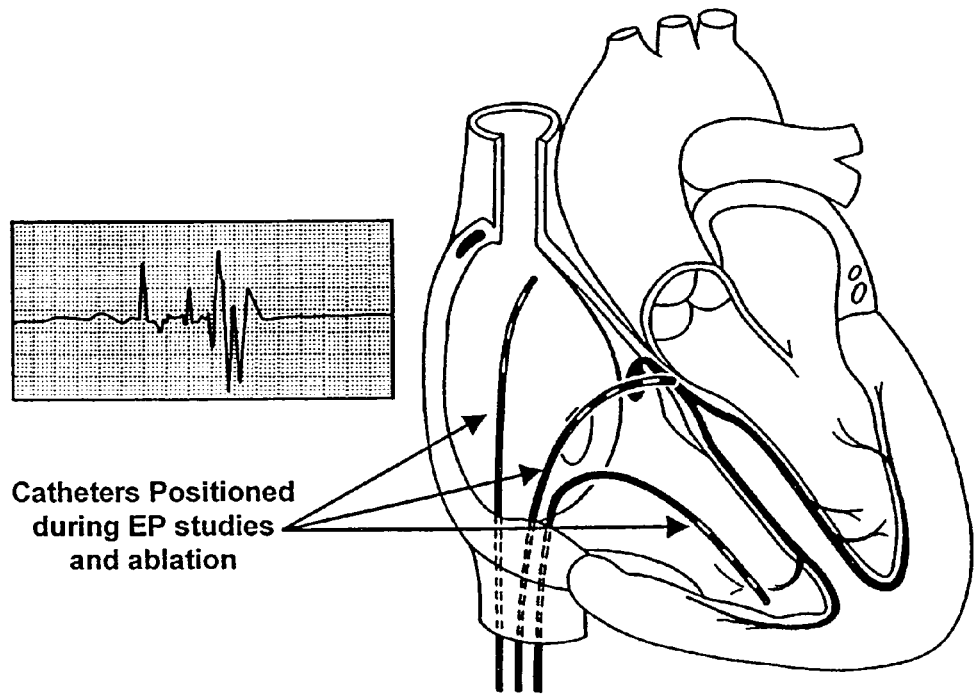
FIG. 2 is a schematic view similar to FIG. 2 illustrating a technique used in electrophysiological studies where catheters are positioned in various locations in the heart and recordings are obtained from these sites.

As shown in FIG. 2, during electrophysiological studies, intracardiac catheters are positioned in the high right atrium, His bundle region and the right ventricle. Programmed delivery of electrical impulses in various chambers can help initiate the clinical rhythm problems in the laboratory. An attempt is then made to move the ablation catheter to the desired location and the procedure of ablation is performed. This technique is adequate only in patients who have sustained stable rhythm problems which can allow movement of catheters sequentially. In patients with arrhythmias like AF, the rhythm becomes unstable immediately, usually following a single premature beat, and cannot be mapped using this technique.

Figure 3:
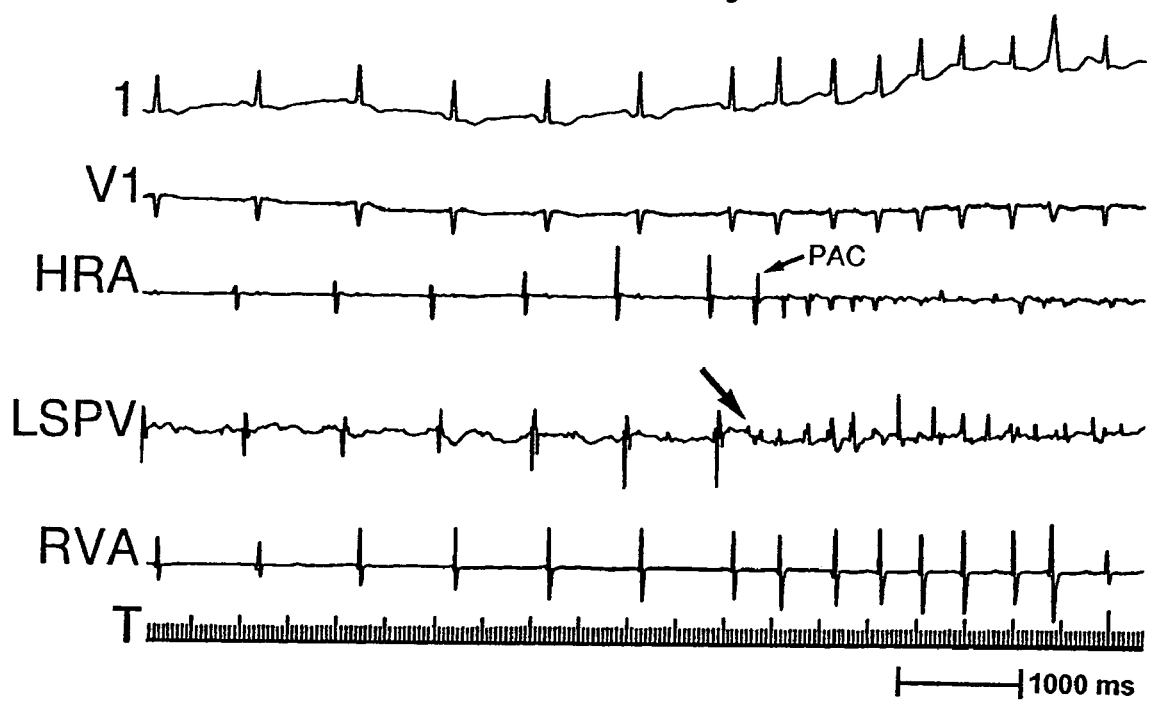
FIG. 3 is an exemplary chart illustrating surface ECG leads and intracardiac (inside the heart) recordings during initiation of atrial fibrillation (AF).

An example of intracardiac recordings and spontaneous initiation of AF is shown in FIG. 3. Three ECG leads and intracardiac recordings from the high right atrium and the right ventricle are seen. A mapping and ablation catheter is positioned in the left superior pulmonary vein. A spontaneous premature atrial contraction (PAC) originating from the left superior pulmonary vein (as shown by the arrow) initiates a paroxysm of AF. However, the standard catheter currently available cannot easily map either the unstable rhythm or the pulmonary vein-left atrial junction through which the premature beat moves to initiate AF because of the complex 3D geometry of these cardiac areas. Furthermore, since these premature beats are not reproducible, the concept of anatomical isolation of left atrial-pulmonary vein junction is extremely important in treating AF.

There is a heterogeneous muscle fiber orientation in the left atrium. These muscle fibers extend into the pulmonary veins (predominantly into the superior veins) in a circular and longitudinal fashion. Once initiated, the premature atrial contractions, being more prone to originate in the pulmonary veins, travel rapidly into the left atrium through the muscle fibers, precipitating AF. A mode of therapy such as a catheter that conforms to the 3D geometry of the left atrium has obvious advantages as it will quickly and effectively isolate these areas.

A cardiac CT is performed to create a 3D image of the left atrium of a patient's heart. Other imaging techniques such as magnetic resonance imaging or ultrasound can be used in place of CT. Following 3D reconstruction of the left atrium, a segmentation process is used to extract the inner surface of the left atrium. The junction between the two pulmonary veins and the left atrium can therefore be easily viewed. Once the 3D image of the left atrium has been acquired, this image can be registered upon an interventional system.

A mapping and ablation catheter can then be visualized upon the interventional system over the registered CT image. Ablation and other relevant spots can be tagged on the CT image as the catheter moves around as illustrated by the circular tags seen in FIG. 4C. The following is a more detailed explanation of this process. Although, for the purpose of clarity, the role of CT imaging is described in the subsequent discussion, the features and concepts outlined can be applied to other imaging techniques known to those skilled in the art, such as MRI and ultrasound.

After obtaining a volume of imaging data of the heart using a CT scan, a 3D image of a specific area of the heart, such as the left atrium, is created using a protocol that is optimized for this cardiac chamber. An example of available software for accomplishing this is the CardEP protocol developed by GE Medical Systems. The remaining cardiac chambers are eliminated and only the left atrium is seen. A detailed 3D image of the left atrium and the pulmonary veins, including endocardial or inside views, is then created as shown in FIG. 4A. The distance and orientation of the pulmonary veins and other strategic areas can be calculated in advance from this 3D image to create a roadmap for use during the ablation procedure.

This 3D image can be stored in a variety of formats to a database. Such formats include DICOM images and geometric wire mesh models. The apparatus for database storage may be hard drives or CD-ROMs.

The 3D image is then registered with a real-time image visualized upon an interventional system. A detailed description of the registration process has been published in several previous reports as, for example, Van den Elsen PA et al., "Medical image matching—a review with classification," *IEEE Engineering In Medicine and Biology,* 12:26-39, 1993 and Fitzpatrick et al., "Image Registration," *Handbook of Medical Image Processing and Analysis,* 2(8): 447-506, Ed., Milan Sonka and J. Michael Fitzpatrick.

Cost function and similarity measures can be used to denote how well the images generated by the CT scan are registered with the coordinates of the interventional system being used. External or internal fiducial markers can be used to identify the location of anatomical landmarks on both the CT image and the real-time image on the interventional system. Registration is achieved by minimizing the mean square distance between the corresponding points.

There are several cardiac interventional systems currently available that can track mapping and ablation catheters in real-time using a variety of different techniques. Any of these systems can be used to register the CT image upon it and then track the catheter over the registered image.

One of these technologies, LocaLisa (Medtronic Inc., Minneapolis, Minn.), uses 1 mA current electromagnetic fields at approximately 30 kHz emitted from cutaneous patches placed on the subject's chest. These patches are positioned to create a three-dimensional axis system. Catheters in the subject's heart receive these signals, and, from the magnitude of the signals, the catheter's position can be determined.

As seen in FIGS. 4A, 4B and 4C, although the localization and navigation of a current catheter over a registered left atrial image has advantages, point by point navigation, ablation and tagging of ablation spots will still be very time consuming. Furthermore, many gaps will be left between the ablation spots created by the catheter that can lead to other rhythm problems.

A catheter apparatus in accordance with this invention has a mapping and ablation catheter that conforms to the true 3D geometry of the left atrium and shortens the AF ablation procedure time needed, making it more efficient and having fewer risks when the catheter is navigated inside the left atrium. This is illustrated in FIG. 5. The distance and orientation of the pulmonary veins and other relevant structures can first be calculated from the left atrial CT image. The catheter can then be rotated, oriented and navigated toward these structures for ablation. Moreover, the catheter can be adjusted and oriented to conform to the left atrial-pulmonary vein junction.

Figure 6:
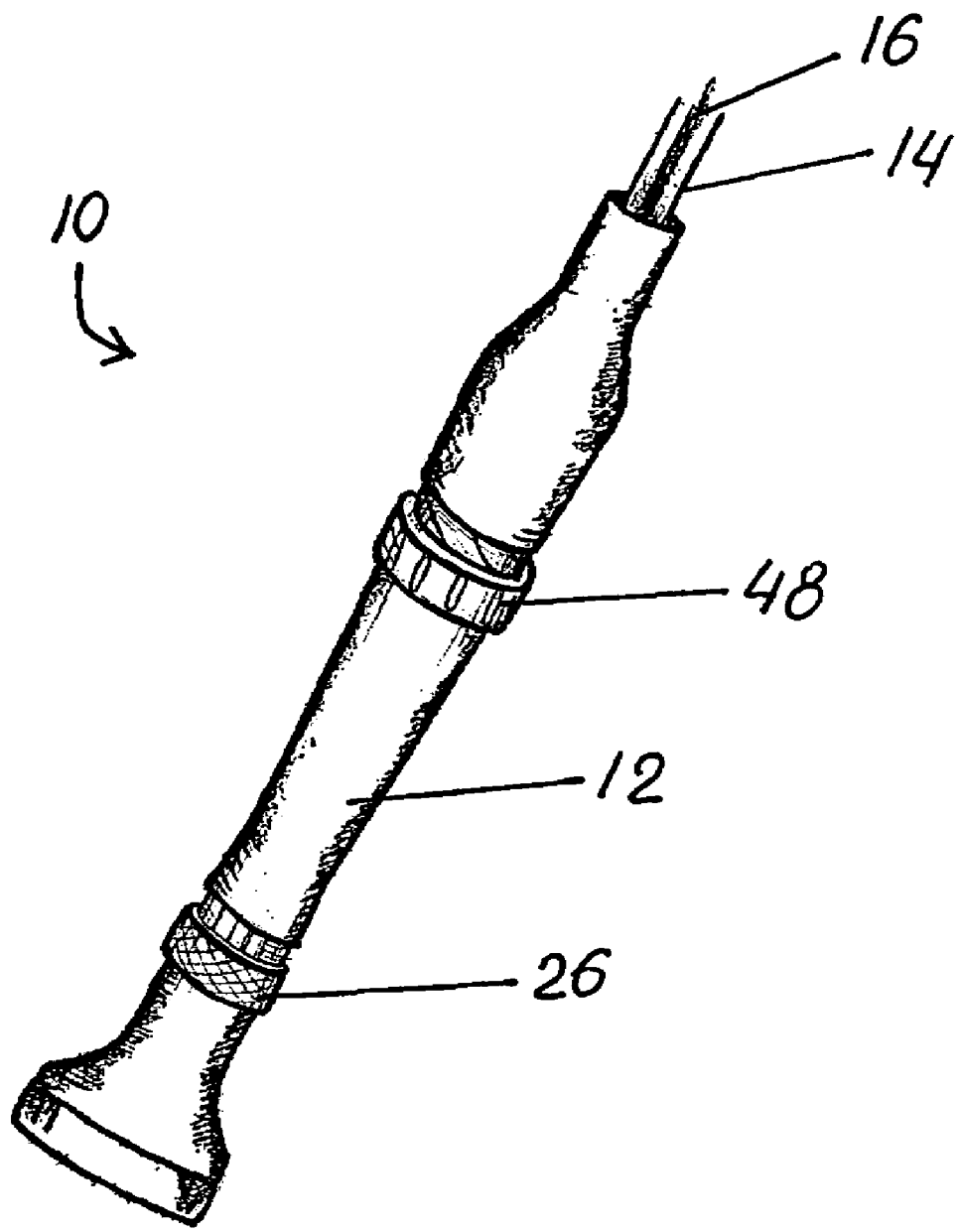
FIG. 6 is a perspective view of a preferred steering handle for the catheter shaft and mapping and ablation catheter in accordance with this invention.

Referring to FIG. 6, a catheter apparatus 10 in accordance with this invention is shown. The catheter apparatus 10 includes a control mechanism, preferably a steering handle 12, a catheter shaft 14, and a mapping and ablation catheter 16. The internal wiring and controls for catheter shaft 14 and catheter 16 will be described in detail below. Catheter shaft 14 extends from the steering handle 12 and encloses catheter 16. Catheter shaft 14 provides support for catheter 16 as catheter shaft 14 is inserted into the patient's left atrium using a standard technique for gaining access such as transeptal catheterization. It is contemplated by the inventor that at least three different lengths for catheter shaft 14 shall be utilized depending upon the height of the patient and size of the left atrium.

Figure 7:
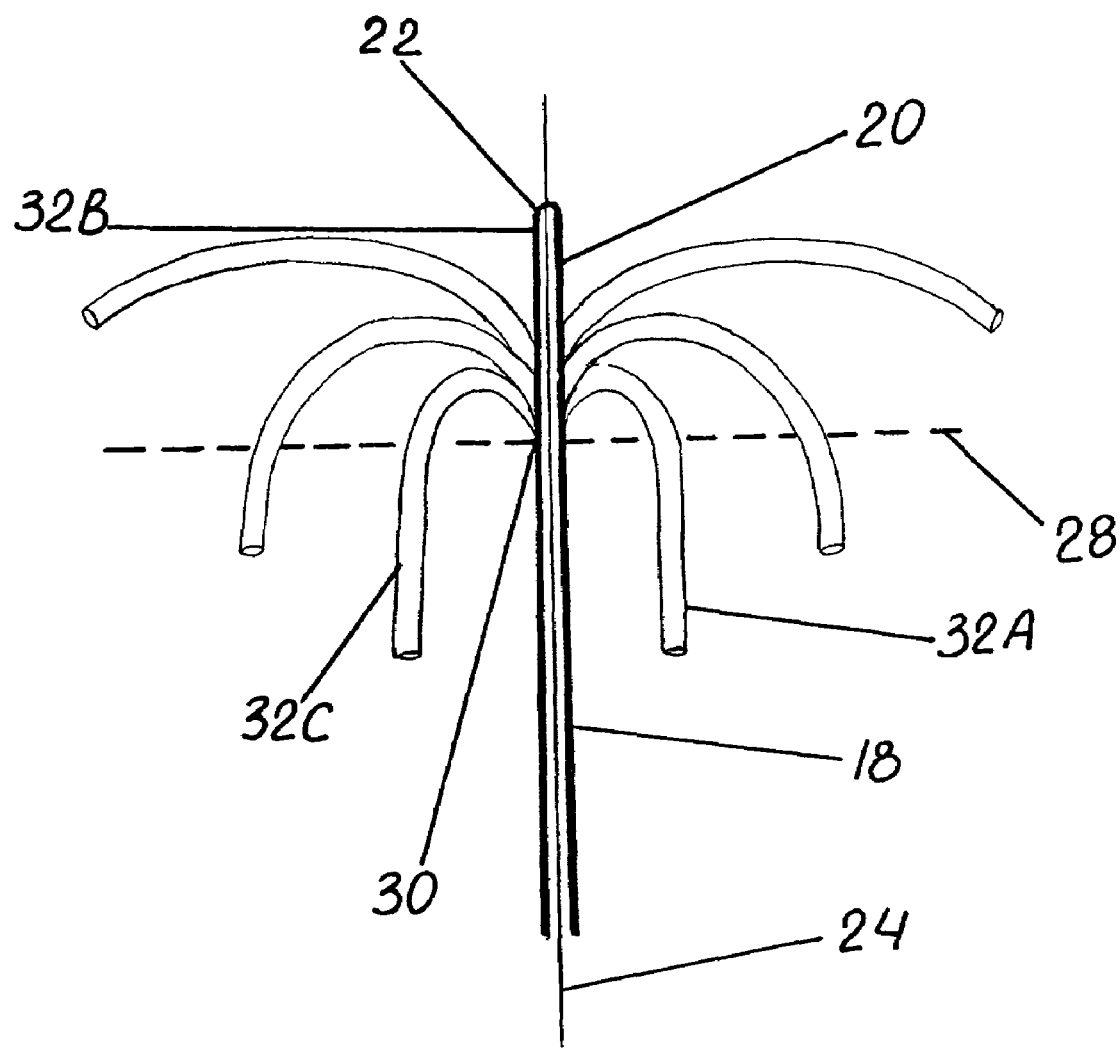
FIG. 7 is a side view of a catheter shaft in accordance with this invention and illustrating movement of the catheter shaft away from the central axis.

FIG. 7 illustrates that catheter shaft 14 has a main body 18 and tip section 20. Tip section 20 is firmly secured to main body 18 and is preferably integral with main body 18. Tip section 20 may vary in length from 1.5 inches to 3.0 inches depending upon the size of the left atrium in which catheter apparatus 10 is being used. Tip section 20 extends outward to a distal end 22. Preferably, distal end 22 is radio-opaque to enable it to be visualized in real-time with x-ray imaging. One or more markers (not shown) on catheter shaft 14 that can also be visualized individually upon the interventional system are desirable. The location of these markers can then be calculated in relation to one or more different points upon the registered CT image.

As shown in FIG. 7, catheter shaft 14 extends along a central axis 24. Tip section 20 is rotatable about central axis 24. The rotation of tip section 20 about central axis 24 along with controlled deflection of tip section 20 away from central axis 24 allows the interventionalist to control the orientation of catheter 16 when extended into the left atrium as described further below.

Steering handle 12 is shown in FIG. 6 as having a first actuator 26. First actuator 26 can be rotated clockwise and counter-clockwise as well as axially along steering handle 12. As illustrated in FIG. 7, rotation of first actuator 26 controls deflection of tip section 20 relative to a plane 28 orthogonal to central axis 24 at transition point 30. Transition point 30 is the junction between main body 18 and tip section 20. Tip section 20 can be deflected 90° above or below plane 28. Longitudinal movement of first actuator 26 controls axial rotation of tip section 20. Rotation of tip section 20 and the angled movement of tip section 20 relative to plane 28 allows tip section 20 to be moved posteriorly, anteriorly, laterally and other directions with respect to plane 28 such that a 360° range of rotation in selected orientations can be achieved.

Rotation of first actuator 26 in a clockwise direction from the neutral position results in deflection of tip section 20 up to a 180° angled curve (32A) from the position where tip section 20 is substantially coaxial (32B) with main body 18. As seen in FIG. 7, tip section 20 can be deflected in this manner into a configuration where it is parallel with main body 18. Rotation of first actuator 26 in a counter-clockwise direction from the neutral position results in a deflection (32C) of tip section 20 of up to 180° away from the coaxial configuration (32B) but in an orientation that is opposite to but coplanar with the arc of deflection of tip section 20 in position 32A.

Advancing first actuator 26 distally forward from the neutral position rotates tip section 20 clockwise 90°. Retracting first actuator 26 backwards from the neutral position will then rotate tip section 20 counter-clockwise 90°.

This multi-directionality of catheter shaft 14 and the ability to bend tip section 22 in a 90° angle above and below plane 28 (with resulting curvature having different radii) enables catheter shaft 14 to be oriented in the direction of the appropriate pulmonary vein when it is inserted into the left atrium.

As illustrated in FIGS. 8 and 9, mapping and ablation catheter 16 includes an electrode section 34 having one or more electrodes 36. Three electrodes, for example, are shown in FIGS. 8B, 9A and 9B. Electrodes 36 are spaced apart by spacer sections 38. Preferably, each electrode 36 is approximately 4 mm. in length while each interelectrode spacer section 38 is approximately 2 mm. Electrodes 36 are assembled at their desired positions along catheter 16 and are fabricated from commercially available conductive material such as platinum, alloy or copper. Further coating can be performed using platinum, gold or iridium.

In a preferred embodiment of the mapping and ablation catheter 16, each electrode 36 is configured to ablate heart tissue. Each electrode 36 is independently operable such that any combination of one, two or three of electrodes 36 can be used to ablate heart tissue during a interventional procedure utilizing catheter apparatus 10.

FIG. 9B shows that each electrode 36 includes a temperature recording site 40 and a bipolar electrogram recording site 42. Each site uses standard sensors. Temperature recording site 40 enables the temperature to be recorded from the tip of each electrode 36 while electrogram recording site 42 enables an electrogram to be obtained in a bipolar fashion.

FIGS. 8A and 8B illustrate movement of electrode section 34 of catheter 16 out of catheter shaft 14. In the position shown in FIG. 8A, only the first distal electrode 36 is seen extending past distal end 22 of catheter shaft 14. When catheter 16 is fully extended from catheter shaft 14, as shown in FIG. 8B, catheter 16 takes on a circular curve, forming a loop 44. Loop 44 is formed by the pre-stressed curve of electrode section 34. The curvature of electrode section 34 enables electrode section 34 to align with the curved inner wall of the left atrial-pulmonary vein junction. Depending upon the number of electrodes 36 in contact with left atrial tissue, one or more electrodes 36 can be used to ablate the heart tissue.

When fully deployed from catheter shaft 14, proximal and distal ends of catheter 16 are adjacent to each other as illustrated in FIG. 8B. In addition, loop 44 is formed at a right angle to catheter shaft 14 to enable electrode section 34 to ablate a ring around the junction between a pulmonary vein and the adjacent atrial wall. FIG. 8B shows that catheter 16 also includes a non-ablating section 46 proximal to electrode section 34. Non-ablating section 46 also provides for the pre-stressed curvature of catheter 16. No electrodes are situated within non-ablating section 46 so that it has no function in the recording or ablation process performed by catheter 16.

As seen in FIG. 6, steering handle 12 also includes a second actuator 48 that controls the movement of mapping and ablation catheter 16 out from and back into catheter shaft 14 and the curvature of catheter 16. Advancing second actuator 48 distally forward extends catheter 16 outward from catheter shaft 14 while longitudinally moving second actuator 48 backwards retracts catheter 16 into shaft 14. Rotation of second actuator 48 adjusts the shape of catheter 16. Preferably, three separate curves of 10 mm., 15 mm. and 20 mm. in diameter can be achieved by rotating second actuator 48. These different curvatures enable catheter 16 to be adjusted for different left atrial sizes and different pulmonary vein dimensions.

Steering handle 12 includes locking mechanisms (not shown) that secure catheter shaft 14 and catheter 16 in a desired curve and position once the proper orientation of catheter 16 has been achieved through movement of first actuator 26 and second actuator 48. This is accomplished by connecting a locking switch to the respective actuator and turning the switch to its locked position when the desired location of each actuator has been achieved.

Catheter shaft 14 is preferably made of a commercially available flexible material such as polyurethane. The size of catheter shaft 14 is preferably 8 French. Nylon can be added to increase the shaft's strength. Increased flexibility of catheter shaft 14 at tip section 20 can be achieved by reducing or eliminating any stiffening material.

Three sets of wires 50, 52, and 54 are anchored to the interior of catheter shaft 14 as illustrated in FIGS. 10A and 10B. Each set of wires is electrically non-conducting and preferably fabricated from material such as nitinol or steel. Wires 50, 52, and 54 are bound to catheter shaft 14 by thermal bonding. Changing the thickness of wires 50, 52, and 54 at tip section 20 and their length along steering handle 12 where each is coupled to first actuator 26 helps in the multi-directional and rotational movement at distal end 22 of catheter shaft 14. Presence of spring-like wiring at the site of bending and rotation of catheter shaft 14 further helps define these movements.

Figure 11A:
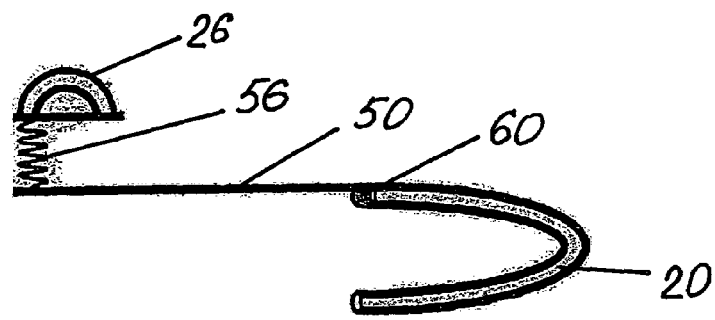
FIGS. 11A, 11B and 11C are a series of schematic views depicting movement of the tip section of the catheter shaft as controlled by the steering handle.
Figure 11B:
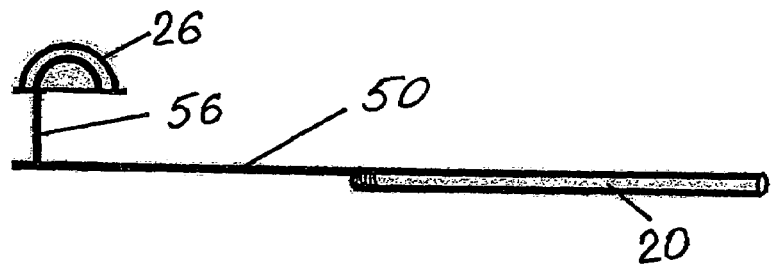
Figure 11C:
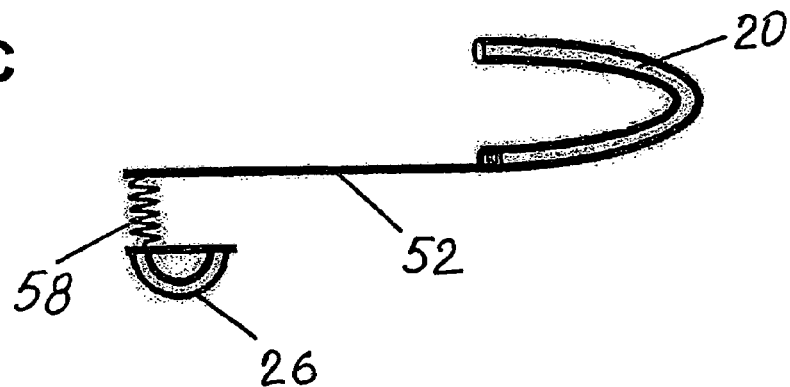

Tip section 20 of catheter shaft 14 is formed, preferably molded, in such a manner that it has a natural tendency to take a shape where it is parallel to main body 18 as shown in FIGS. 11A or 11C. Steering wires 56 and 58 connect wires 50 and 52 respectively to first actuator 26. When tip section 20 is in the coaxial position seen in FIG. 11B, steering wires 56 and 58 are kept taught. In rotating first actuator 26 in a clockwise or counter-clockwise direction as illustrated in FIGS. 11A and 11C, the respective steering wire 56 and 58 is slackened. This enables tip section 20 to return to its preformed shape.

Wire 54 is connected to spring-like wire 60 at transition point 30. Wire 54 is connected to first actuator 26 by steering wire 62. Tip section 20 is formed, preferably molded, in such a manner that it has a natural tendency to return to its original radial position when it is rotated 90° clockwise or counter-clockwise by action of wire 60 and then released. Longitudinal movement of first actuator 26 forward and back actuates rotation of tip section 20 clockwise and counter-clockwise respectively through the slackening and stiffening of steering wire 62 and wire 54.

Figure 12:
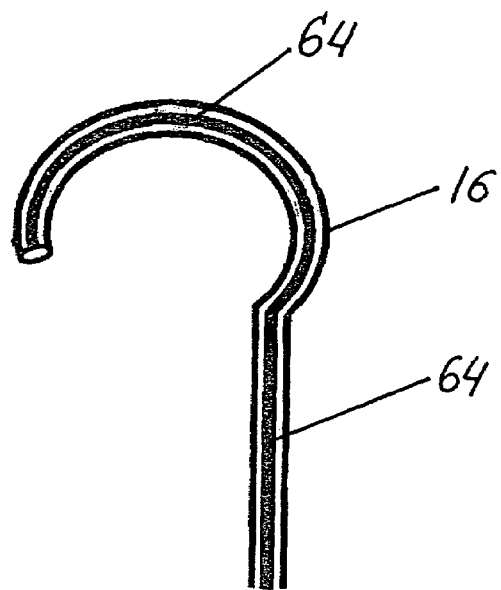
FIG. 12 is a schematic view of the catheter depicting the pre-stressed curve and spline.

The size of catheter 16 is preferably 7 French. The pre-stressed curve of catheter 16 is achieved with an elongated member or spline 64 as illustrated in FIG. 12. Spline 64 is made up of inert wires from a material having memory shape such as, for example, nitinol. The stiffness and curve of catheter 16 can be altered by varying the amount of the material used in spline 64. The pre-stressed curve of spline 64 is accomplished by molding spline 64 to the desired curve at the time of manufacturing. The area of the curve on spline 64 is somewhat thinner and not as stiff as the remaining portion of spline 64. This allows for maneuverability and malleability of the curve on catheter 16.

Figure 13:
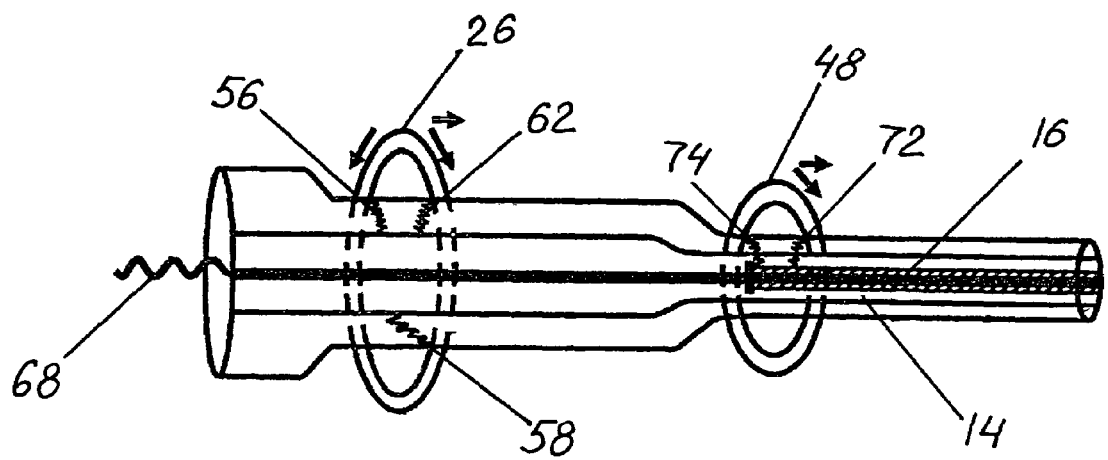
FIG. 13 is a schematic view of the steering handle.

Conductive wires 66 are coupled to electrodes 36 to conduct energy such as radio-frequency energy for performing ablation within the heart. Delivered energy can also be microwave energy or cryo-energy. Wires 66 run through the interior of catheter 16 and are connected through steering handle 12 to a connector 68 as shown in FIG. 13. Connector 68 is connected in turn to the source of energy that is being delivered. FIGS. 14A and 14B show how wires 66 and spline 64 are placed inside the body of catheter 16. The portion of catheter 16 carrying wires 66 is surrounded by a non-conductive sleeve made of commercially available material such as polyurethane or nylon. An additional non-conducting wire 70 is connected to second actuator 48 and enables the diameter of the pre-stressed curve of catheter 16 to be adjusted.

Steering handle 12 is hollow and has an inner lumen large enough to accommodate catheter shaft 14 as well as the various steering wires as depicted in FIG. 13. Second actuator 48 controls the axial movement of catheter 16 and the diameter of the pre-stressed curve of catheter 16 through steering wires 72 and 74 that are coupled to catheter 16 and wire 70 respectively. The diameter of the pre-stressed curve is controlled by steering wire 74 coupled to wire 70 as illustrated in FIGS. 15A and 15B. By rotating second actuator 48 in a clockwise direction as shown in FIG. 15B for positions A, B and C, the diameter of the pre-stressed curve is changed as the tension on steering wire 74 is relieved.

Figure 16:
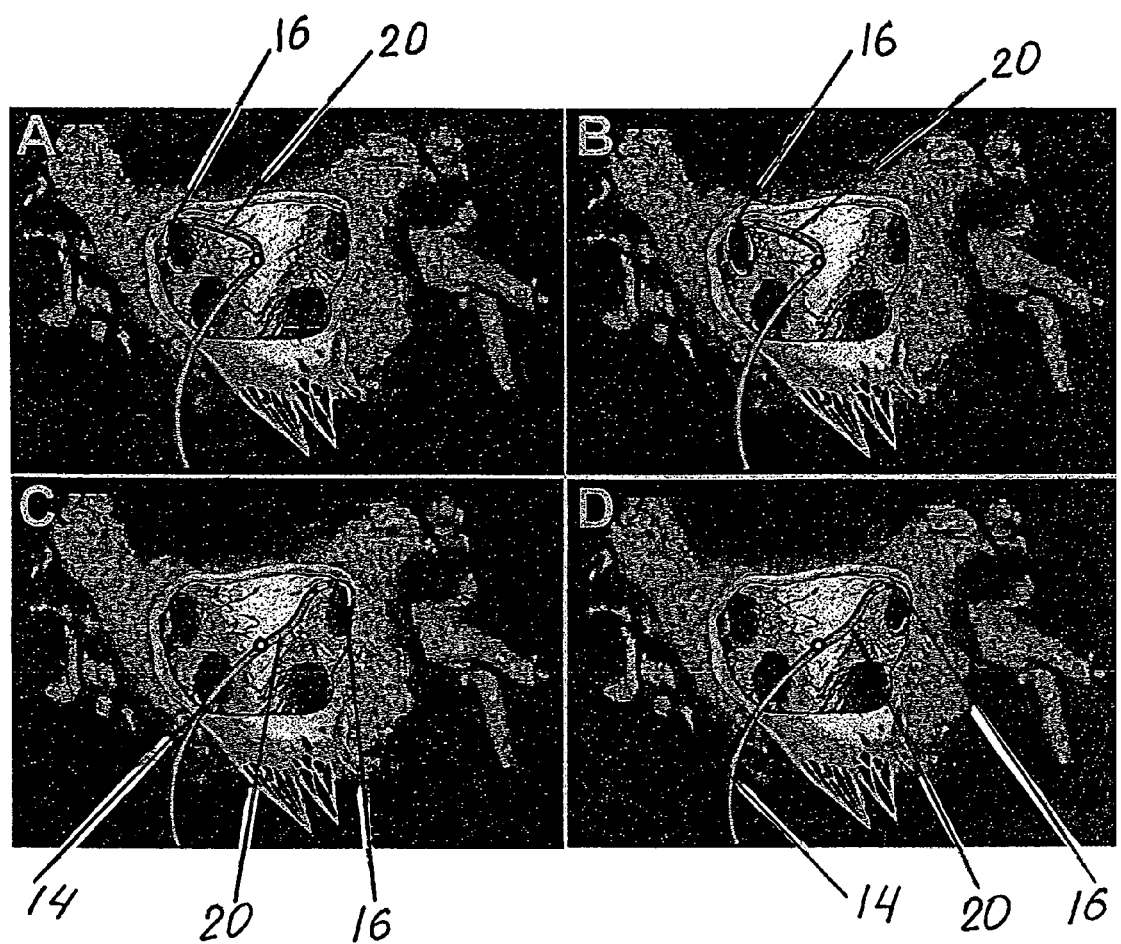
FIG. 16 is a sequential illustration of the movement of the catheter shaft and catheter as it conforms to the 3D geometry of the left atrium.

FIG. 16 illustrates, as an example, the introduction of a catheter shaft of the present invention into the left atrium using the transeptal approach and shows how the catheter apparatus conforms to the 3D left atrial anatomy. FIG. 16 presents the anterior view of the left atrium with the right pulmonary veins on the left side and left pulmonary veins on the right side. As illustrated, catheter shaft 14 can be adjusted to achieve different curve angles and orientations depending upon the pulmonary veins which need to be accessed. Once catheter shaft 14 has been placed in the desired orientation, the mapping and ablation catheter 16 can be extended outward from the catheter shaft 14 to ablate the desired areas.

Pulmonary veins can be isolated separately or together and as far away as desired from ostium of the pulmonary veins. Similarly catheter 16 can be used to ablate other areas such as between the pulmonary veins and mitral annulus, connecting the pulmonary veins, and isolating the left atrial appendage. It can be seen that this invention allows for an appropriately tailored approach to the AF ablation procedure. In choosing the right approach to AF ablation, the duration of the procedure is reduced and the efficacy improved.

It will be appreciated that automatic techniques may be employed to perform any of the steps previously mentioned by using one or more of the several computer-assisted methods available for the detection, localization, visualization and movement of a catheter. Moreover, these methods can be completely automatic or interactive with input from the user. Furthermore, the features described may improve with user input and interaction.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. In particular, although the preceding description discusses the left atrium with reference to AF, it is understood that the invention could be utilized for other rhythm problems and other chambers.

It will be further appreciated that in one aspect of this invention, the process of imaging and registration can be completely eliminated. In such instances, the physician can choose a catheter apparatus in accordance with this invention that will best fit a particular patient and have navigation of that apparatus achieved using currently available imaging techniques such as fluoroscopy or other modalities available in the art.

The invention claimed is:

1. A catheter apparatus of the type used in the treatment of heart arrhythmia comprising:
    a catheter shaft having a main body and a coaxial tip section joined to the main body, the tip section having a tip distal end and being rotatable about a central axis and deflectable such that the tip section can be selectively curved away from the main body;
    a mapping and ablation catheter slidably disposed within the catheter shaft, the mapping and ablation catheter having a catheter distal portion, the catheter distal portion being a pre-stressed curve whereby the mapping and ablation catheter curves as the catheter distal portion is extended axially from the catheter shaft and when the catheter distal portion is fully extended from the catheter shaft, all of the curve is substantially coplanar with a plane substantially perpendicular to the central axis at the tip distal end; and
    a control mechanism coupled to both the catheter shaft and the mapping and ablation catheter whereby the control mechanism controls, with respect to the central axis, selective rotation and selective deflection of the tip section and controls selective axial movement of the mapping and ablation catheter with respect to the catheter shaft.

2. The apparatus of claim 1 wherein the curve forms a loop when the catheter distal portion is fully extended from the catheter shaft.

3. The apparatus of claim 2 wherein the loop has a diameter ranging from 10 mm. to 20 mm.

4. The apparatus of claim 2 wherein the loop has a selectively variable diameter and the control mechanism controls the diameter of the loop.

5. The apparatus of claim 4 wherein:
    the control mechanism is a steering handle;
    the steering handle has a first actuator mechanically connected with respect to the catheter shaft whereby actuation of the first actuator can independently rotate the tip section about the central axis and deflect the tip section away from the central axis; and
    the steering handle has a second actuator mechanically connected with respect to the mapping and ablation catheter whereby actuation of the second actuator can independently move the mapping and ablation catheter axially within the catheter shaft and control the diameter of the loop formed by the mapping and ablation catheter.

6. The apparatus of claim 5 wherein the catheter apparatus is adapted to be displayed, when positioned in a chamber of the heart, over a 3D model registered with an interventional system, the 3D model being created from cardiac image data obtained from a medical imaging system, whereby the catheter apparatus can be navigated within the heart utilizing the registered 3D model.

7. The apparatus of claim 6 wherein the medical imaging system is a computer tomography (CT) system.

8. The apparatus of claim 7 wherein the heart arrhythmia is atrial fibrillation and wherein the 3D model is of the left atrium and pulmonary veins.

9. The apparatus of claim 6 wherein the mapping and ablation catheter has an electrode section at a distal end of the mapping and ablation catheter, the electrode section having a plurality of electrodes, and at least one electrode being adapted to take intracardial recordings of electrical activity and display the recordings on the interventional system.

10. The apparatus of claim 5 wherein the mapping and ablation catheter includes a spline.

11. The apparatus of claim 10 wherein the spline is fabricated from nickel-titanium having shape memory.

12. The apparatus of claim 1 wherein the catheter distal portion has an electrode section, the electrode section having a plurality of electrodes wherein each electrode is operable to ablate a selected area of heart tissue brought into contact with the electrode.

13. The apparatus of claim 12 wherein at least two electrodes are independently operable.

14. The apparatus of claim 12 wherein each pair of electrodes is separated by a non-ablating section.

15. The apparatus of claim 12 wherein each electrode includes a temperature recording site and an electrogram recording site.

16. The apparatus of claim 1 wherein the tip section is joined to the main body at a transition point, the tip section is pre-stressed to form a substantially 180° curve with respect to the central axis at the transition point, the curve being substantially coplanar with the main body, and the control mechanism controls selective straightening of the tip section.

17. The apparatus of claim 1 wherein the heart arrhythmia is atrial fibrillation.

* * * * *